(12) United States Patent
Power et al.

(10) Patent No.: US 7,941,396 B2
(45) Date of Patent: May 10, 2011

(54) PROCESS CONTROL METHOD WITH INTEGRATED DATABASE FOR ELECTRONICALLY DOCUMENTING THE CONFIGURATION, MODIFICATION AND OPERATION OF A CONTROLLED PROCESS

(75) Inventors: Michael A. Power, Irvine, CA (US); Richard Kramer, Sharon, MA (US)

(73) Assignee: Symbion Systems, Inc., Irvine, CA (US)

( * ) Notice: Subject to any disclaimer, the term of this patent is extended or adjusted under 35 U.S.C. 154(b) by 543 days.

(21) Appl. No.: 10/832,001

(22) Filed: Apr. 26, 2004

(65) Prior Publication Data

US 2005/0038565 A1 Feb. 17, 2005

Related U.S. Application Data

(60) Provisional application No. 60/465,312, filed on Apr. 25, 2003.

(51) Int. Cl.
*G06F 7/00* (2006.01)
*G06F 17/00* (2006.01)
(52) U.S. Cl. ........................................ 707/601; 707/602
(58) Field of Classification Search .................. 707/601, 707/602
See application file for complete search history.

(56) References Cited

U.S. PATENT DOCUMENTS

| | | | | |
|---|---|---|---|---|
| 5,249,260 A | * | 9/1993 | Nigawara et al. | 706/45 |
| 5,325,522 A | * | 6/1994 | Vaughn | 707/1 |
| 7,123,974 B1 | * | 10/2006 | Hamilton | 700/87 |
| 2002/0023083 A1 | * | 2/2002 | Durkalski | 707/3 |
| 2003/0069795 A1 | * | 4/2003 | Boyd et al. | 705/22 |
| 2003/0088324 A1 | * | 5/2003 | Hamelink | 700/90 |
| 2003/0135500 A1 | * | 7/2003 | Chevrel et al. | 707/9 |
| 2004/0015521 A1 | * | 1/2004 | Hudicka | 707/200 |

OTHER PUBLICATIONS

U.S. Appl. No. 60/465,312, filed Apr. 2003, Power, Michael A., 707/9.*
"Guidance for Industry, Part 11, Electronic Records; Electronic Signatures—Scope and Application.", Aug. 2003, pp.1-9, US Food & Drug Administration.

* cited by examiner

*Primary Examiner* — Cam Y Truong
*Assistant Examiner* — Michael Pham
(74) *Attorney, Agent, or Firm* — Joseph C. Andras; Myers Andras & Sherman LLP

(57) ABSTRACT

A process control method that automatically and comprehensively manages the creation, storage and use of electronic records during the operation of a controlled process and for governing and documenting the users that operate the computer systems that are involved in the creation, storage and use of the electronic records. The method controls a process, such as a chemical process, by receiving measurement information relating to the process, applying rules to the received measurement information to determine a desired response, and sending control information to at least one device associated with the process, so as to modify the process. The method maintains the rules, measurements and control activity in transaction logs or audit trails related thereto in a secure database. By providing convenient, centralized control of the process within a secure database, the method enhances compliance with the FDA regulations that permit electronic records to be regarded as the equivalent to paper records under 21 CFR Part 11.

5 Claims, 9 Drawing Sheets

PROCESS CONTROL METHOD WITH INTEGRATED DATABASE FOR ELECTRONICALLY DOCUMENTING THE CONFIGURATION, MODIFICATION AND OPERATION OF A CONTROLLED PROCESS

PRIORITY CLAIM

This patent application claims the benefit of the priority date of U.S. Provisional Patent Application Ser. No. 60/465,312, filed on Apr. 25, 2003 and entitled SECURITY GUARD ARCHITECTURE FOR PROCESS ANALYSIS SYSTEM pursuant to 35 USC 119. The entire contents of this provisional patent application are hereby expressly incorporated by reference.

FIELD OF THE INVENTION

The present invention relates generally to process control equipment and methodology. The present invention relates more particularly to a process control method that automatically and comprehensively manages the secure creation, storage and use of electronic records relating to the operation of the process. The process control method may be embodied in process control system wherein measurement information is received via a network, rules are applied to the received measurement information to determine a desired response, and control information representative of the desired response is sent via the network to facilitate control of at least one control device.

BACKGROUND OF THE INVENTION

The Food and Drug Administration (FDA) is the federal body that "is responsible for protecting the public health by assuring the safety, efficacy, and security of human and veterinary drugs, biological products, medical devices, our nation's food supply, cosmetics, and products that emit radiation." (FDA Mission Statement).

In order for the FDA to execute its mission of ensuring the public health and safety as related to food and drugs, numerous persons involved with the production of pharmaceuticals, chemicals, and the like, are required by statute or regulation to maintain records or submit information to the FDA.

As computers have become ubiquitous and their storage capacity has increased many times over, it has become increasingly common for such persons to want or even have to create, store and submit electronic records or information in lieu of paper records or information.

In March of 1997, in response to this continuing change in the manner of keeping and submitting records, the FDA issued final regulations that provide criteria for FDA acceptance, under certain circumstances, of electronic records as equivalent to paper records. The FDA issues all of its governing regulations within Title 21 of the Code of Federal Regulations (CFR). The new electronics records regulations were issued as 21 CFR Part 11, or simply "Part 11." The 21 CFR Part 11 regulations became effective in August 1997.

21 CFR Part 11 imposes specified controls and requirements onto the creation, storage, and use of electronic records. The intent was to make electronic records useable in lieu of paper records. Nonetheless, there has been a great deal of uncertainty as to how to how best comply with Part 11. This is especially true in the process control and data analysis context since the configuration and use of equipment and the associated collection, recordation, analysis, and process control use of data has been accomplished with a disjointed collection of electronic records and paper records that are created and used in a myriad of different ways during the operation of the process and, moreover, a disjointed collection of users that create and use such records, by and large, independently of any computer system that may be involved in storing of such records.

There remains a need, therefore, for a system that automatically and comprehensively manages the creation, storage and use of electronic records during the operation of a controlled process and for governing and documenting the users that operate the computer systems that are involved in the creation, storage and use of the electronic records and the changes that such users make to the process.

As further background, systems for controlling processes are well known. A large variety of different processes are used in the manufacturing and testing of products such as pharmaceuticals, petroleum derivatives, chemicals, materials, integrated circuits, semiconductors, foods, cosmetics, automobiles, consumer electronics and many other items. Both manual and automatic control systems for such processes are commonly used.

Manual control systems are operated by a person. The person monitors the process and makes adjustment thereto as needed. Because manual control systems are operated by a person, they are subject to error and inconsistency. Manual control systems are subject to error because people are subject to making errors. People are also subject to fatigue, which increases the likelihood of error. Manual control systems are subject to inconsistency because people inherently rely upon subjective decision making processes.

Automatic control systems are operated by a machine, such as a microcontroller or general purpose computer. The machine monitors the process and makes adjustment thereto as needed. Because automatic control systems are operated by a machine, they are generally less subject to error and inconsistency than are manual control systems. Generally, a machine can be made to perform a task in a precise and reliable manner, such that errors are minimized. Machines are not subject to fatigue in the same sense that people are, so machines are not generally more likely to make errors after a long shift. Automatic control systems are less subject to inconsistency than people because machines can be made to rely upon objective decision making processes.

A control system, whether manual or automatic, generally receives at least one input which is representative of some parameter associated with the process. Based upon the value of the parameter, decisions are made regarding if and how the process is to be modified. These decisions are generally made according to predetermined rules.

The number of inputs to a control system can be large and the amount of data associated with such inputs can be large. The rules for determining desired responses to the inputs can be complex, especially when there are many ways in which the process can be modified. The time allowed for making a decision can be very small. Typically, the cost of providing a machine to operate an automatic control system is less than the cost of providing a person to manually control the same process. In many instances, these factors necessitate that a machine be used for process control.

Because of these and other advantages of automatic control systems, the use of machines to control processes is widespread. However, although contemporary automatic control systems have proven generally suitable for their intended purposes, they possess inherent deficiencies which detract from their overall effectiveness and desirability. For example, many times it is desirable to control one or more processes from a computer that is located remotely with respect to where the process is being performed. However, according to contemporary practice, the distance between a computer that is controlling a process and the process itself is limited.

In an attempt to facilitate such remote control of a process, a computer can be wired so as to provide communication with one or more measurement devices (devices which monitor the process) and one or more control devices (devices which are being controlled as part of the process).

For example, a process control computer located in a chemist's office can be wired so as to receive input signals from several spectrometers which are located on the production floor of a pharmaceutical manufacturing facility. The same process control computer can be wired so as to provide output signals to flow control valves located on the same production floor or elsewhere. The process control computer may be hundreds of feet from the spectrometers and/or the flow control valves. Indeed, the process control computer does not even have to be located in the same building as the spectrometers and/or flow control valves.

While such interconnection of the computer, the spectrometers, and the flow control valves does provide enhanced functionality with respect to control systems that required a dedicated microcontroller or other type of collocated control device, such interconnection suffers from inherent disadvantages.

For example, the lengths of the wires from the spectrometers to the computer and the lengths of the wires from the computer to the flow control valves are limited. Unless some type of repeater, amplifier, or signal conditioning device is utilized, the distance between the computer and either the spectrometers or the flow control valve generally cannot be greater than several hundred feet. The use of such repeater, amplifier, or signal conditioning devices is generally undesirable because of the expense associated therewith, the reliability thereof, and/or the inherent signal delays caused thereby.

As such, although the prior art has recognized, to a limited extent, the problem of controlling processes from diverse locations with respect to measurement devices (such as spectrometers) and control devices (such as flow control valves), the proposed solutions have, to date, been ineffective in providing a satisfactory remedy. Therefore, it is desirable to provide a process control system wherein the measurement devices and the control devices may generally be disposed at any desired location and the computer or other controller thereof may generally be located at any other desired location.

BRIEF SUMMARY OF THE INVENTION

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112.

The present invention specifically addresses and alleviates the above mentioned deficiencies associated with the prior art. More particularly, the present invention comprises a method for controlling a process, wherein the method comprises receiving measurement information via a network, applying rules to the received measurement information to determine a desired response, and sending control information via the network. The control information facilitates control of at least one control device according to the desired response.

These, as well as other advantages of the present invention, will be more apparent from the following description and drawings. It is understood that changes in the specific structure shown and described may be made within the scope of the claims, without departing from the spirit of the invention.

BRIEF DESCRIPTION OF THE DRAWINGS

The invention and its various embodiments can now be better understood by turning to the following detailed description of the preferred embodiments, which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
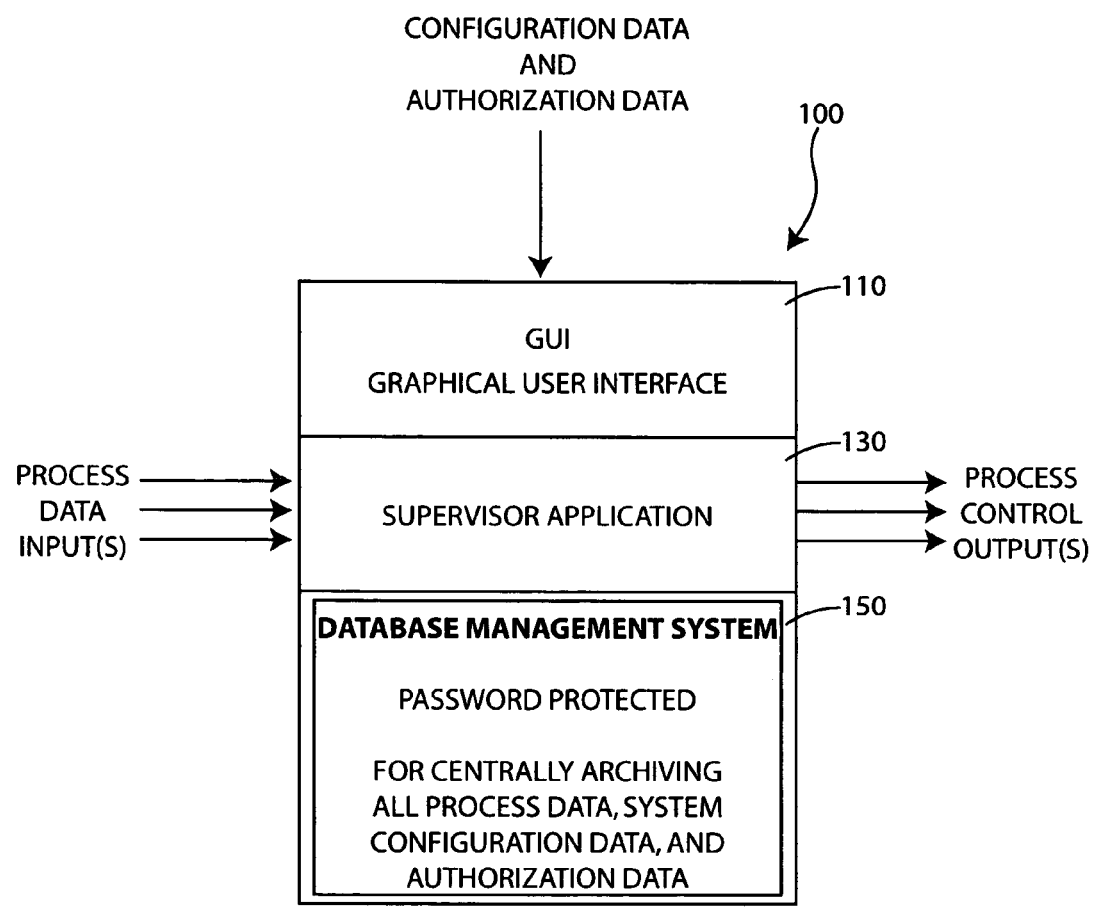
FIG. 1 illustrates a process control system 100, and method of using the same, according to a first preferred embodiment of the invention.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus, if an element can be understood in the context of this specification as including more than one meaning, then its use in a claim must be understood as being generic to all possible meanings supported by the specification and by the word itself.

The words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

Thus, the detailed description set forth below in connection with the appended drawings is intended as a description of the presently preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions may be accomplished by different embodiments that are also intended to be encompassed within the spirit of the invention.

A method for controlling a process includes receiving measurement information relating to the process via a network, applying rules contained within "configurations" to the received measurement information to determine a desired response, and sending control information via the network to at least one device associated with the process, so as to modify the process. The control information facilitates control of the device(s) according to the desired response.

Preferably, the measurement information and the rules are stored in a common database. Alternatively, the measurement information, the rules, and/or the administrative information are stored in two or more different databases.

Preferably, the measurement information, the rules and administrative information are all stored in a common database and access to the database is limited to authorized users. As those skilled in the art will appreciate, storing the measurement information, the rules, and the control information in a common database advantageously simplifies management of this information in a manner which facilitates easy access to and use of the information and also facilitates security management thereof.

Access to the database(s) is preferably limited to authorized users by comparing a log-in name and password to a list of authorized users and their passwords. Alternatively, various other methods for authenticating the authorization of users may be employed. For example, biometric sensors such as fingerprint readers, face recognition equipment, and/or retina scanners may be used to verify the identity of a user.

Preferably, the integrity of an older or first database (containing measurement information, rules, and/or control information) is maintained when a newer or second database is desired, such that the first database is still available to provide a history of the operation of the process control provided by the present invention. That is, whenever it is desirable to create a new database, such as when the rules are changed, then a new database is created, but the old database is kept. In this manner, the measurement information, the rules, and the control information relating to past tests can be recalled, as desired. As those skilled in the art will appreciate, access to such historic process information can be important in determining the cause of process failures, in enhancing the efficiency of processes, in developing new processes, and in defining new rules to control processes.

The integrity of a first database is preferably maintained by archiving the first database when a modification thereof is desired, such that the first database remains available for review. A second database is then formed from the first database (such as by making a copy of the first database). The second database is modified so as to form the desired new database, such as by changing the rules therein. The second database is then used for process control.

Preferably, a time stamp and a user name are associated with modifications to the database. Preferably, a transition log stores an audit trail which provides information relating to modifications of the database. The transition log stores information such as the user name of the person who modified a database, the date and time of the modification, and any comments that the user desires to add (such as the reason for the modification). Preferably, the transition log is accessible only to authorized users.

Preferably, the measurement information is received via an Ethernet and the control information is sent via the Ethernet. Preferably, the measurement information is received via the Internet and the control information is sent via the Internet. However, as those skilled in the art will appreciate, the measurement information and the control information may be communicated by any desired network or combination of networks. Indeed, the measurement information and the control information may be communicated over different networks, different combinations of networks, or different portions of a common network.

Preferably, the measurement information is received from at least one measurement device having an Internet Protocol (IP) address and the control information is sent to at least on control device having an IP address. That is, according to the preferred embodiment of the present invention, the measurement devices have IP addresses and the control devices have IP addresses. The process controller of the present invention also preferably has an IP address. The use of IP addresses for the measurement devices, the control devices and the process controller facilitates communication via the Internet.

The IP addresses of the measurement devices, the control devices and/or the process controller may optionally be IP addresses of general purpose computers or other devices associated therewith. Thus, the measurement devices, the control devices and/or the process controller may communicate through such computers or other devices.

Alternatively, the IP addresses may be for the measurement devices, the control devices and/or the process controller themselves. Thus, the measurement devices, the control devices and/or the process controller may communicate directly over the network, and not through a general purpose computer.

As a further alternative, the measurement devices, the control devices and/or the process controller may comprise Bluetooth compliant devices or the like and thus may communicate via radio frequency (RF) with a general purpose computer or other device which then relays communications to the network.

Thus, the process control system of the present invention and the process(es) being controlled thereby preferably have IP addresses. Preferably, the measurement devices and control devices have separate IP addresses. However, the measurement devices and the control devices may have a common IP address, such that both the measurement devices and the control devices communicate via a common controller, computer, or other device.

For example, a plurality of measurement devices and a plurality of control devices may be configured to communicate with a common general purpose computer which has a single IP address. The computer may then be configured to communicate with the process control system of the present invention via the Internet using a single IP address. Indeed, the computer may facilitate the control of a number of different related or unrelated processes by providing such communication with the process control system of the present invention.

Preferably, the measurement information is representative of at least one measurement of an analytical instrument. For example, the measurement information may comprise measurements made using spectrometers, gas chromatographs, temperature sensors, pressure sensors, weight sensors, optical sensors, timers, flow sensors, current sensors, voltage sensors, capacitance sensors, inductance sensors, electric field sensors, magnetic field sensors, specific gravity sensors, and/or concentration sensors. Indeed, the measurement information may comprise information from a large variety of different types of sensors or other devices. The above listed sensors and devices are thus by way of example only and not by way of limitation. A single process may be controlled via the use of one sensor or a plurality of sensors (which may be all of one type or of any desired combination of types).

Optionally, at least a portion of the information representative of at least one measurement is analyzed so as to facilitate control of at least one control device. For example, the results of a spectrometer measurement may be analyzed to determine if a particular substance is present in a sample. If the substance is present in the sample, then a flow control valve may be operated to modify the flow of a fluid so as to desirable affect a process.

For example, the spectrometer may be configured to determine if undesirable contaminants are present in a fluid feed line. Fluid flow through the fluid feed line can then be terminated if the presence of a particular contaminant is found or if the concentration of the contaminant exceeds a predetermined level.

According to the present invention, a user defines the rules that are used to determine a desired response to the received measurement data. Preferably, these rules are defined via the use of scripting in order to create so-called "configurations." A copy of the *Symbion Programmers Guide Version* 1.0 accompanies this patent application and its entire contents are hereby incorporated by reference. Those skilled in the art will appreciate that various other methods for defining the rules are likewise suitable.

The rules may also be defined on a general purpose computer by dragging and dropping graphic symbols representing measurement devices and/or graphic symbols representing control devices. Preferably, in such case, the rules are further defined by dragging and dropping graphic symbols representing methods associated with or properties of the measurement devices and/or control devices. Parameters may be applied to the graphic symbols, such as by clicking thereon and entering the desired information.

Thus, according to one aspect, the present invention comprises storing administrative information in a database, storing rules in the database, receiving measurement information, storing the received measurement information in the database, applying the rules to the measurement information to determine a desired response, and sending control information to at least one control device. The control information facilitates control of at least one control device according to the predetermined desired response. The administrative information, the rules, the received measurement information, and a history of the sent control information, are preferably stored in the same database.

According to one aspect, the present invention comprises a process controller comprising a general purpose computer configured to communicate via a network and also comprises a database. The database preferably contains administrative information, rules for determining a desired response to measurements, measurement information, and a history of responses provided by the process controller. Thus, the database contains a log of measurements and corresponding control information. The computer is configured to receive measurement information via the network, apply the rules to the received measurement information to determine a desired response and send control information via the network.

According to one aspect, the present invention comprises a process control system comprising at least one measurement device, at least one control device, and a process controller. The process controller preferably comprises a general purpose computer configured to communicate via a network and a database containing rules for determining a desired response to measurements. The computer is configured to receive measurement information from at least one measurement device via the network, apply the rules to the received measurement information to determine a desired response and send control information to at least one control device via the network.

The control devices, for example, comprise valves, heaters, coolers, mixers, current sources, voltage sources, electric field sources, magnetic field sources, and lasers. Indeed, the control devices comprise any devices or equipment that have an affect upon the performance of the process.

FIG. 1 illustrates a process control system 100, and method of using the same, according to a first preferred embodiment of the invention, including the preferred system's three main components, a graphical user interface (GUI) 110 for performing administrative tasks such as inputting authorization data and configuration data, a Supervisor Application 130 that receives process data and outputs process control signals, and a database management system (DBMS) 150 (e.g. MySQL) for secure, centralized archiving of all process data, system configuration data, and authorization data in an effort to fully and automatically comply with the FDA's 21 CFR Part 11 mandate over electronic records.

The GUI 110, supervisor application 130, and DBMS 150 are often situated on the same general purpose computer, but that is not always the case, particularly when the system 100 is deployed in a larger, more distributed environment.

Figure 2:
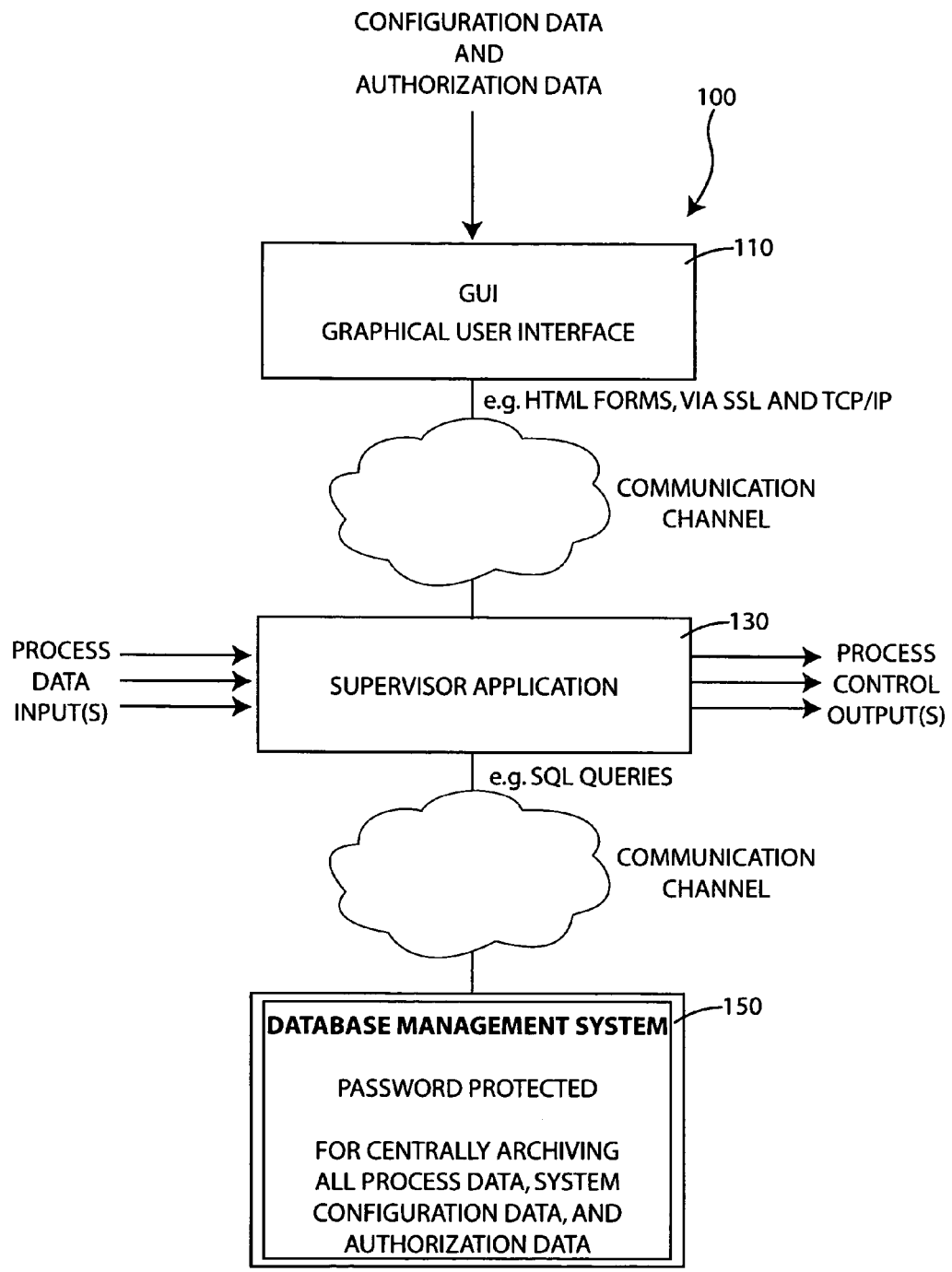
FIG. 2 illustrates the control system 100 of FIG. 1 in a more generalized situation wherein the three main components may reside on different computers that are located in different locations and connected by suitable communication channels.

FIG. 2 illustrates the control system 100 of FIG. 1 in a more generalized situation wherein the three main components may reside on different computers that are located in different locations and connected by suitable communication channels. For example, the GUI 110 may be displayed on a remote computer as a web-based interface that communicates with the supervisor application 130 on an Ethernet channel, using TCP/IP and SSL. In like fashion, the supervisor application 130 may communicate with the database management system 150 using conventional structured query language (SQL) queries via a standard Open DataBase Connectivity (ODBC) interface operating on a suitable intra-computer or inter-computer channel, or equivalent.

Figure 3A:
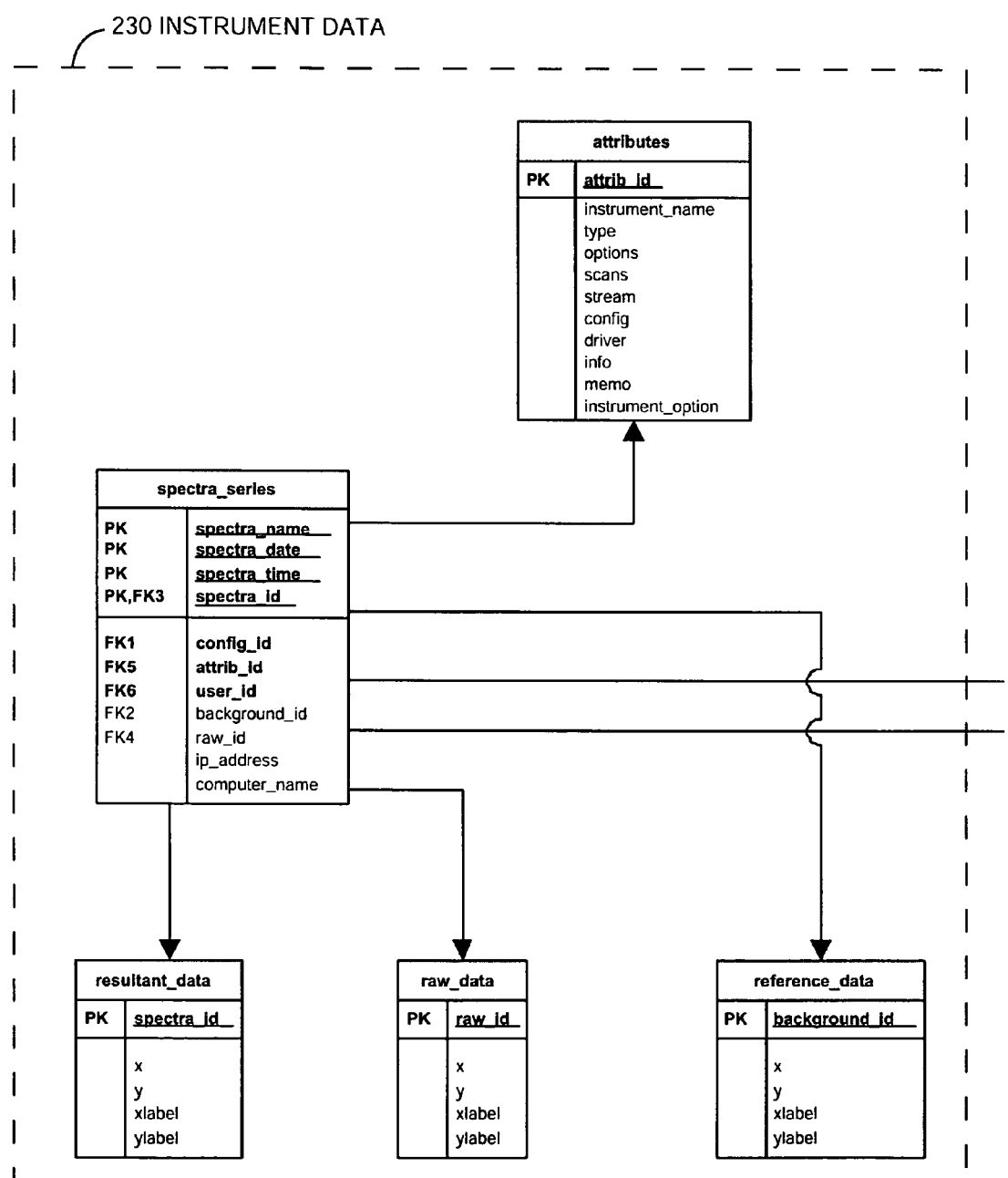
FIG. 3, spanning sheets 3(a) to 3(c), illustrates the presently preferred structure of the relational database 200 accessed by the DBMS 150 of FIGS. 1 and/or 2.
Figure 3B:
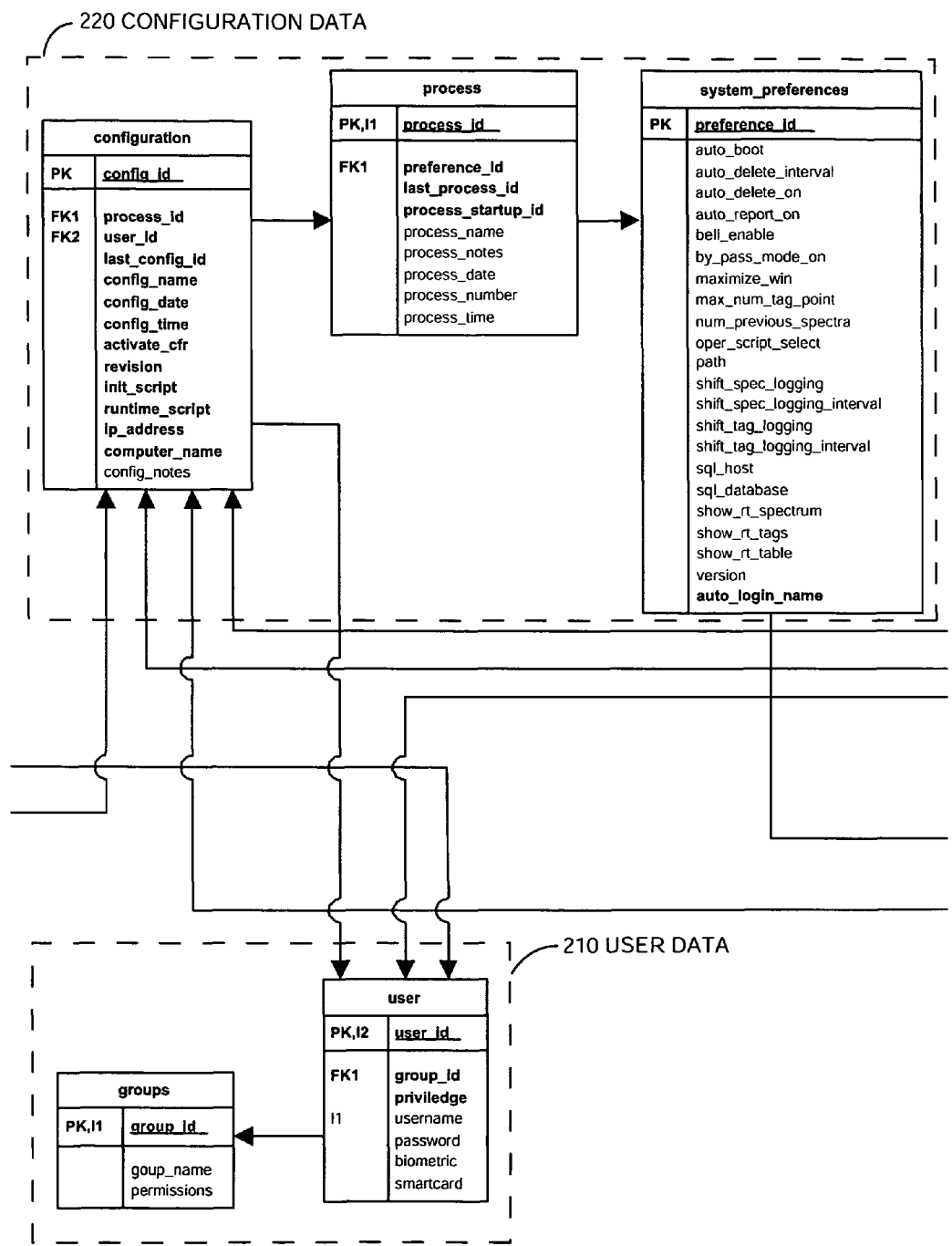
Figure 3C:
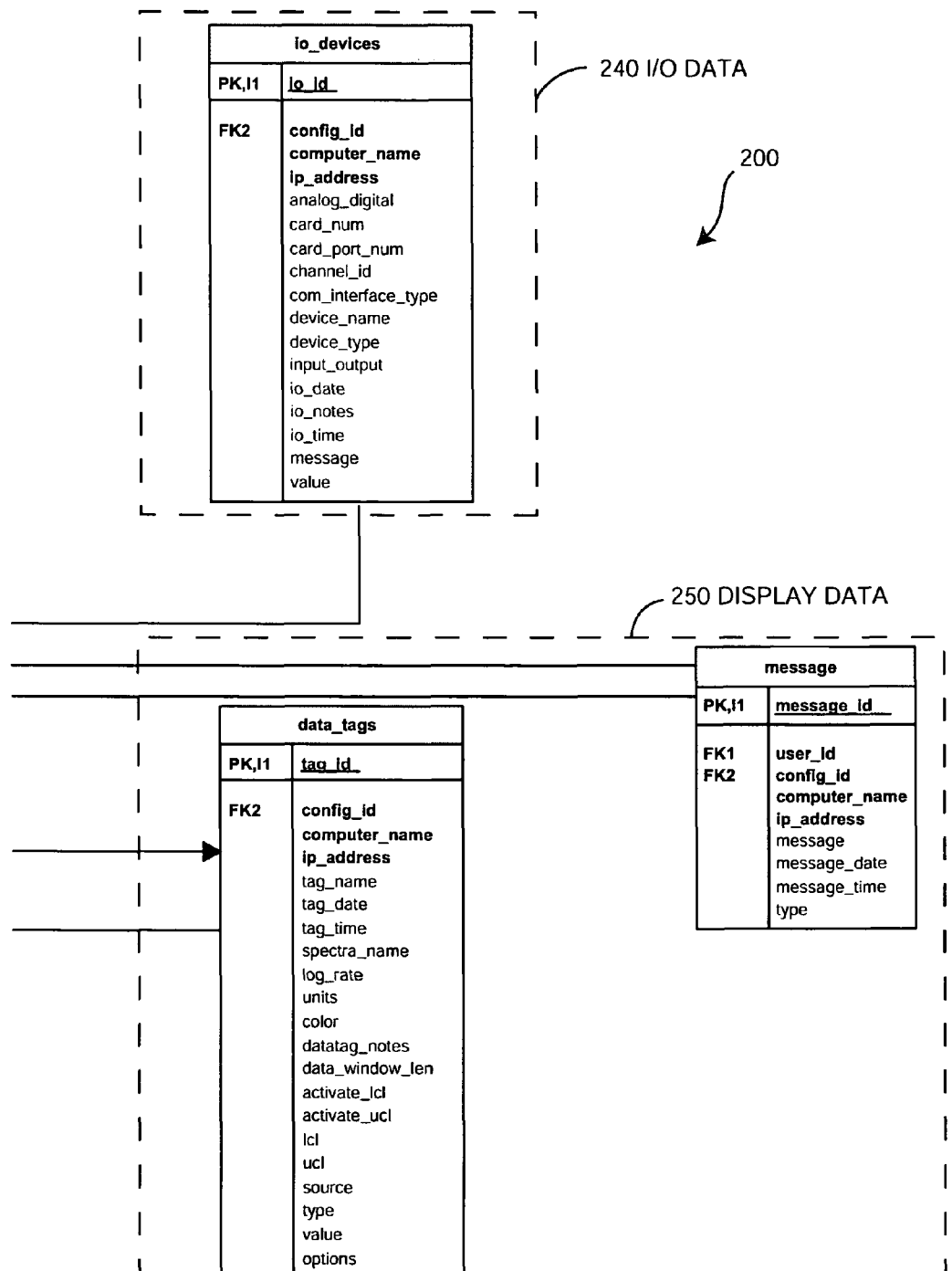

FIG. 3, spanning sheets 3(a) to 3(c), illustrates the presently preferred structure of the relational database 200 accessed by the DBMS 150. The database 200 includes a number of data tables that each contain a number of data entities. In addition, the various data table are associated with one another in various one-to-one and one-to-many relationships as is customary with a normalized relational database design.

From a relatively high level, we can generally classify the data tables into five groups comprising Configuration Data 210, User Data 220, Instrument Data 230, I/O data 240, and display data 250. In more detail, the tables within each group include:

| Table | Description |
|---|---|
| | Configuration Data 210 |
| process | Contains the unique ID and descriptive name of each "process" that has been created by an authorized user. Each process includes one or more "configurations". If the process has two or more "configuration," they run simultaneously, but independently and asynchronously of one another. |
| configuration | Contains the unique ID, descriptive name, and associated scripts related to each "configuration", an executable routine for data collection, data analysis, and process control. Each configuration has two main parts, an Initialization Script that runs only one time at the beginning of the configuration (this script is stored in a text-based field called "init_script"), and a a Runtime Script that runs repeatedly until an exit condition is met (this script is stored in a text-based field called "runtime_script"). The Initialization and Runtime Scripts for a particular configuration are sometimes called an "IR Pair". |
| system_preferences | Contains certain configuration values that are globally defined or common to all IR Pairs for a given process. |
| | User Data 220 |
| groups | Contains various user groups and the permissions that are common to users in each group. |
| User | Contains the username and password pair for each user (plus other optional security data), individually defined privileges, and a relational list to the group table if desired. |
| | Instrument Data 230 |
| attributes | Contains all of the attributes associated with the collection of data, as opposed to the data itself (e.g. how many scans were taken, what driver was used, etc . . . ) |
| spectra_series | A time dependent sequence of spectra. In other words, a series of spectral snap shots of the process that is running. |
| raw_data | This table is provided in case the spectrometer or other instrument returns raw, unprocessed data. |
| reference_data | Contains reference data that was initially collected without a representative sample in order to account for the measuring system's optics, the spectrum of the light source, etc . . . |
| resultant_data | Contains processed data corresponding to a single |

| Table | Description |
|---|---|
| | spectrum, collected with a representative sample and established as a ratio value relative to the data in the reference_data table. |
| | I/O Data 240 |
| io_devices | Contains a record of any analog or digital input or output. In essence, this table provides a historic log of each I/O transaction associated with scalar values - for recording measurements taken and control actions outputs generated. |
| | Display Data 250 |
| data_tags | A collection of time-dependent scalar values that correspond to sample values (e.g. pH, pressure, or temperature) or to analysis of the spectra, that are displayed on the Operational Screen. |
| message | Contains messages that are displayed within a "Message Window". The messages are merely informative, or provide a warning, or indicate an alarm level. |

It is unnecessary to provide a detailed explanation of each data entity since the diagram is somewhat self-documenting and since the precise values tracked may vary from application to application. However, several high level conclusions can be drawn from reviewing FIG. 3 with some accompanying explanation.

First, the data structure 200 limits who may use the system. Second, the data structure 200 consistently, repetitively, and automatically keeps track of who, did what, when, with regard to configuration modifications and/or data acquisition. Third, the data structure 200 archives all data that is collected under the direction of a particular user, pursuant to a particular configuration, for future review if ever necessary.

As to limiting who may use the system, the User Authorization Data 210 defines certain user groups (e.g. admins, power users, and operators) and related permissions and only permits certain specified users who login with a username and a password (biometric inputs, smartcards if desired) to perform the permitted tasks associated with the group or groups of which they are members.

As to keeping track of who, did what, when, the Configuration Data 220 includes a configuration table that includes an auto-incrementing data entity that is labeled "config_id" and defined as a primary key (PK) of that table. In accordance with the control of the DBMS 150 pursuant to suitable code in the Supervisor Application 130, each time the user manually saves a configuration screen, a new record is written to the configuration table by incrementing the config_id value and by recording all other associated values. Thus, the system 100 automatically creates a complete record of all configuration settings that are in effect as of that moment in time, and later when spectra and/or other data is gathered, to serve as an audit trail to enhance compliance with 21 CFR Part 11.

As to archiving all data that is collected under the direction of a particular user, and pursuant to a particular configuration, the Instrument Data 230 includes a spectra_series table that is relationally tied to an attributes table and to several data tables including a resultant_data table, a raw_data table and a reference_data table. Whenever the system 100 causes a connected instrument (e.g. a spectrometer) to measure a sample, the config_id of the associated configuration is automatically stored in the spectra_series table, the instrument's present settings are automatically stored in the attributes table, and the raw data returned by the instrument are automatically stored in the data tables.

FIGS. 4-8 depict an alternative embodiment of the present invention. Although this embodiment is illustrated and described as utilizing the Internet to facilitate communications between the processes control system of the present invention and the individual processes (which comprise measurement devices and control devices) being controlled thereby, any suitable network may alternatively be utilized. Thus, such illustration and description of the network as being the Internet is by way of example only, and not by way of limitation.

Figure 4:
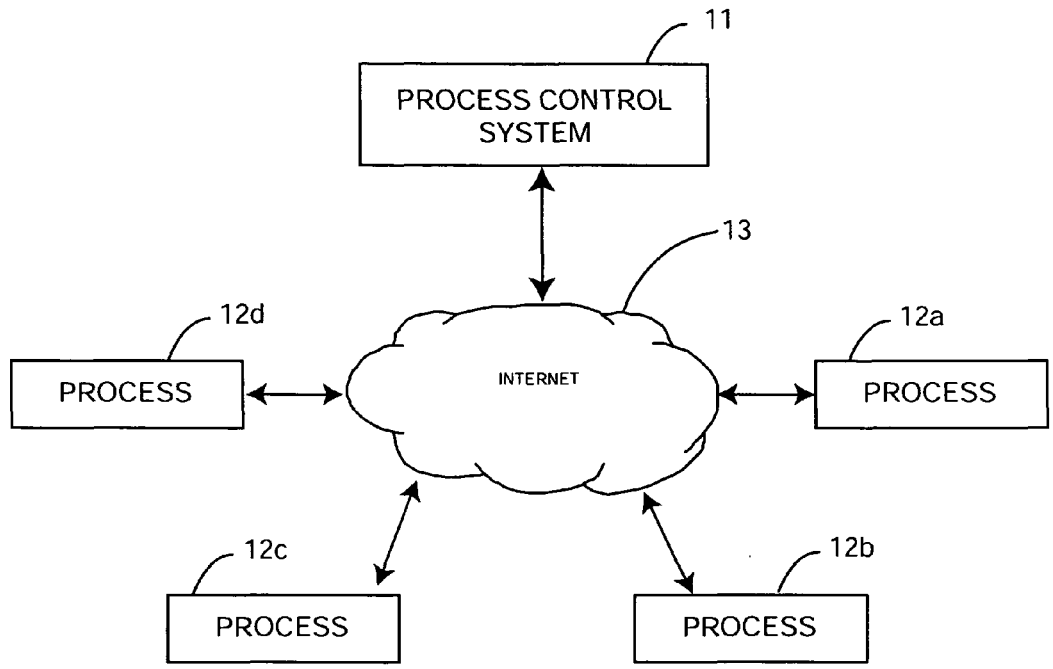
FIG. 4 is a block diagram showing communication between a process control computer and a plurality of processes via a network such as a local area network (LAN), or the Internet, according to an embodiment of the present invention.

Referring now to FIG. 4, the present invention generally comprises a process control system 11, which communicates with at least one process. The process control system 11 preferably communicates with a plurality of separate processes 12a-12d. The structure and operation of the process control system 11 is described in further detail below.

All of the processes 12a-12d may be substantially identical to one another. Thus, each of the processes 12a-12d may comprise different process lines or assembly lines, each of which uses substantially the same types of devices to perform substantially the same types of processes. For example, each of the processes 12a-12d may comprise a process line for making acetylsalicylic acid (aspirin).

Alternatively, each of the processes 12a-12d may be substantially different from one another. Thus, each of the processes 12a-12d may comprise different process lines or assembly lines, each of which uses substantially different types of devices to perform substantially different types of processes. For example, process 12a may comprise a process line for making acetylsalicylic acid, process 12b may comprise a process line for making acetaminophen (Tylenol®), process 12c may comprise a process line for making polyethylene, and process 12d may comprise an assembly line for making computer keyboards.

Indeed, the processes 12a-12d may comprise any desired combination of the same or similar processes and completely dissimilar processes.

The processes 12a-12d may be located at a common facility or may be located at geographically diverse facilities. Indeed, the only limitation placed upon the location of the processes 12a-12d is the extent of the network. With a worldwide network, such as the Internet, each the processes 12a-12d may generally be disposed at any desired location. The process control system 11 may be disposed at any desired location and need not be disposed proximate any of the processes 12a-12d.

As mentioned above, the network via which the process control system 11 communicates with the processes 12a-12d can be any desired network, such as the Internet. Typically, the network comprises an Ethernet network.

Bidirectional communication is facilitated by the network, so that measurement information is communicated from measurement devices associated with each process 12a-12d to the process control system 11 and so that control information is communicated from the process control system 11 to control devices of the processes 12a-12d.

According to the preferred embodiment of the present invention, the process control system 11, some portion thereof, or some device associated therewith has an IP address so as to facilitate communication via the Internet. Similarly, each process 12a-12d, some portion thereof, or some device associated therewith has at least one IP address so as to facilitate communication via the Internet.

Figure 5:
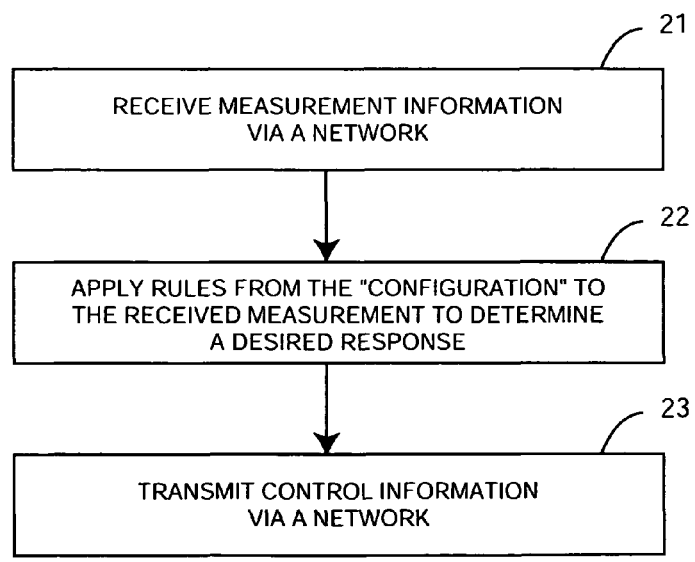
FIG. 5 is a flow chart showing generally the method of controlling a process, according to the present invention.

Referring now to FIG. 5, the method for controlling a process according to the present invention generally comprises receiving measurement information via the Internet, as shown in block 21; applying rules to the received measurement information to determine a desired response, as shown in block 22; and sending control information via the Internet, as shown in block 23.

Measurement information is received by the process control system 11 (FIG. 4) from at least one measurement device associated with at least one process 12a-12d via the Internet. Such measurement devices can comprise sensors, analytic devices, and/or any device which provides information regarding a process being controlled by the process control system 11 of the present invention. One example of such a measurement device is spectrometer 55 of FIG. 8.

The rules applied are generally predefined rules, such that responses which are appropriate with respect to the received measurement information can be quickly and reliably determined therefrom. The rules may comprise fuzzy logic, expert system, neural network, heuristic and/or artificial intelligence based rules or decision making ability.

Control information is sent from the process control system 11 to control devices associated with the processes 12a-12d via the Internet. Such control devices can comprise any devices which affect the performance of a process and/or the outcome of the process. One example of such a control device is flow control valve 56 of FIG. 8.

Figure 6:
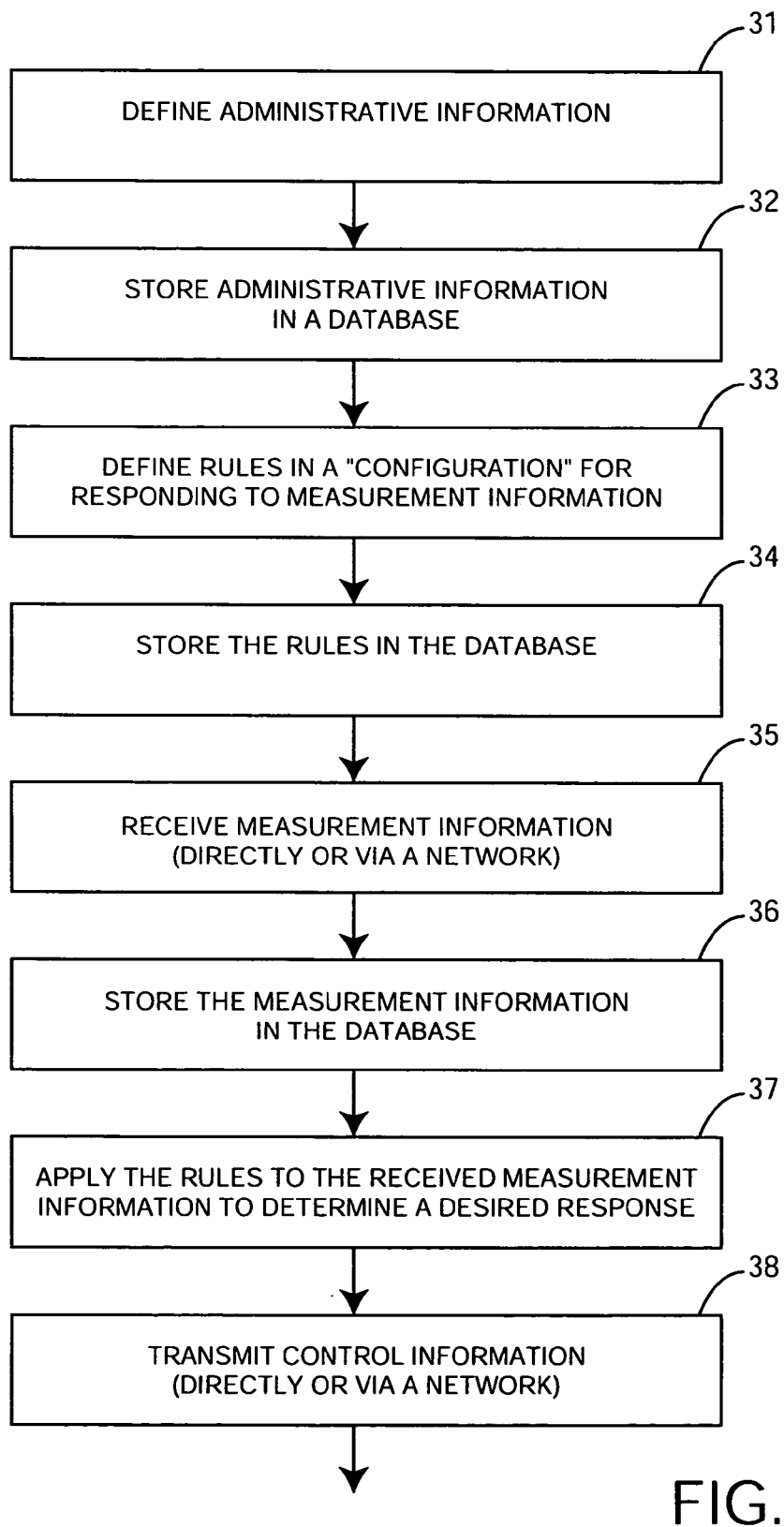
FIG. 6 is a flow chart showing the method of controlling a process of FIG. 5 in further detail.

Referring now to FIG. 6, the method for controlling a process according to the present invention more particularly comprises defining administrative information, as shown in block 31; storing administrative information in a database, as shown in block 32; defining rules for responding to measurement information, as shown in block 33; storing the rules in the database, as shown in block 34; receiving measurement information via the Internet, as shown in block 21; storing the measurement information in the database, as shown in block 35; applying the rules to the received measurement information to determine a desired response, as shown in block 22; and sending control information via the Internet, as shown in block 23.

Defining administrative information comprises defining which users have access to the process control system 11 and what level of access they have. Defining administrative information may also comprise defining passwords for the users, defining how information is displayed on monitors, how information is saved (in which databases), how information is printed (fonts used, size of graphs, units provided in graphs, and format of reports, for example), and/or defining parameters necessary for communication upon the network (such as IP addresses and communication protocols).

Some users may have a level of access which limits them to only observing operation of the process control system 11, without making any changes thereto. For example, such users may be able to observe the measurement information received by the process control system 11, the rules used by the process control system 11, and the control information sent by the process control system 11.

Conversely, other users may have a level of access which allows them to modify operation of the process control system 11. For example, such users may be able to determine what measurements are to be received, define and change the rules used to determine responses to measurement information, and determine what control devices the control information is to be sent to.

The administrative information is stored in a database (such as database 42 of FIG. 7), so that it is readily accessible for use by the process control system 11. Preferably the database is a hierarchical database, such as one of the SQL database products provided by Microsoft Corporation of Redmond, Wash.

Defining the rules for responding to measurement information is preferably performed using a scripting type of tool command language, such as Tcl (which is short for Tool Command Language and is pronounced "tickle"), provided by Scriptics at http://www.scriptics.com/.

The rules are defined so that desired operation of control devices is obtained based upon inputs to the process control system 11 of the present invention from measurement devices associated with a process. For example, the rules may be defined so as to accept inputs from a spectrometer and so as to control a flow control valve, as discussed in detail with respect to FIG. 8 below. As those skilled in the art will appreciate, the rules may be defined to accept inputs from a large variety of different types of measurement devices and so as to provide outputs to a large variety of different types of control devices.

The rules are stored in a database (such as database 42 of FIG. 7), so that they are readily accessible for use by the process control system 11. Preferably, the rules are stored in the same database as the administrative information. Storing the rules in the same database as the administrative information simplifies operation of the present invention by providing a central location for information needed thereby.

Preferably, measurement information is also stored in the same database as the administrative information and/or the rules. Storing measurement information in the same database as the administrative information and the rules further simplifies operation of the present invention.

Preferably, control information (such as the response history 46 of FIG. 7) is also stored in the same database as the administrative information, the rules, and/or measurement information. Storing control information in the same database as the administrative information, the rules, and/or measurement information yet further simplifies operation of the present invention.

Figure 7:
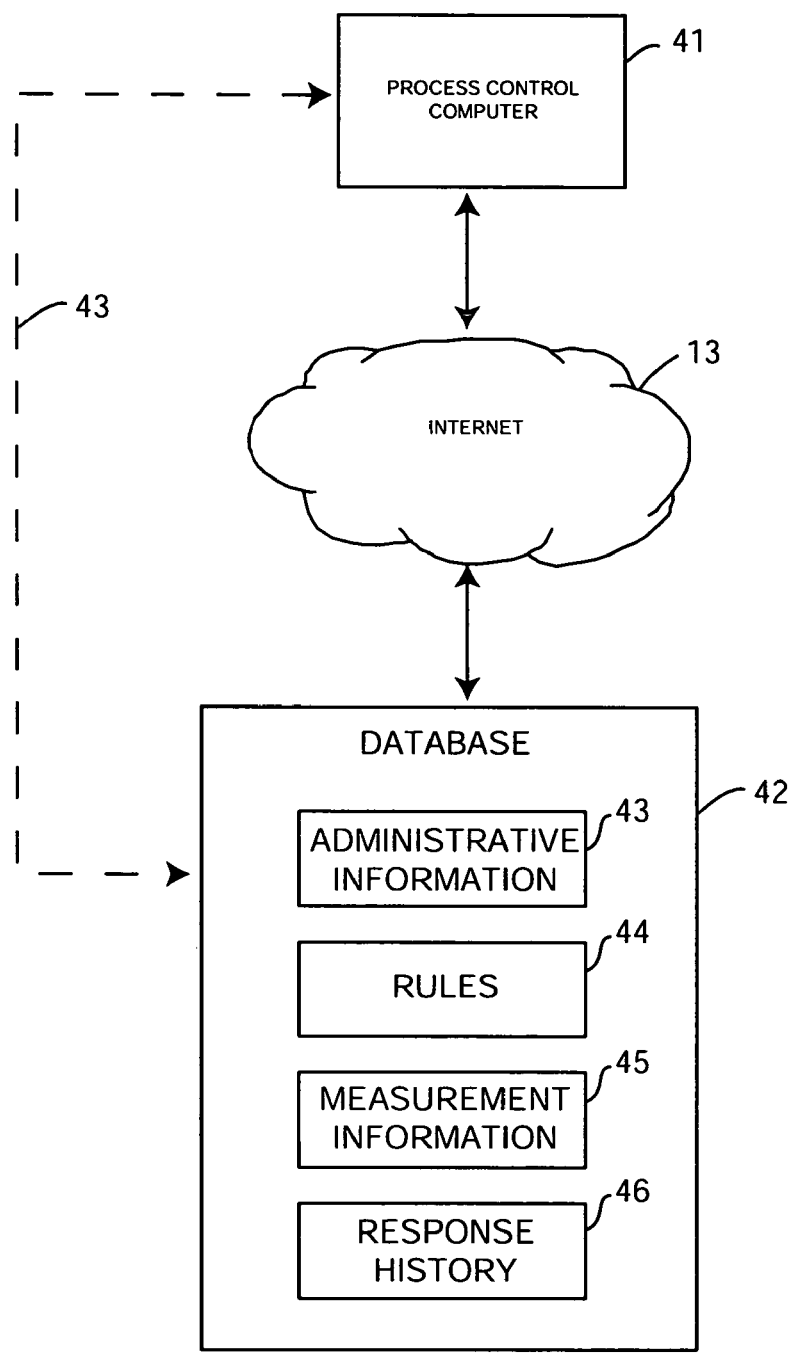
FIG. 7 is a is a block diagram showing the process control system of FIG. 4 in further detail.

Referring now to FIG. 7, the process control system 11 of the present invention comprises a process control computer 41 and a database 42. The process control computer 41 applies the rules to measurement data and determines the desired response thereto. The process control computer may also facilitate the entry of administrative information and/or the rules. Alternatively, administrative information and/or the rules can be entered via a different computer, which is preferably in communication with the process control computer 41, such as via a network.

The process control computer 41 is in communication with the database 42, so as to facilitate the storage of information within the database 42 and so as to facilitate the retrieval of information therefrom. The process control computer 41 may communicate with the database 42 via a network, such as the Internet 13. Thus, the database may be stored within a dedicated server, such as MySQL provided by MySQL AB of Seattle, Wash. and Uppsala, Sweden, or SQL Server provided by Microsoft Corporation of Redmond, Wash.

Alternatively, the database may be more directly coupled to the process control computer, as indicated by bidirectional arrow 43 of FIG. 7. Thus, the database 42 may be hard wired to the process control computer 41. Indeed, the database 42 may be collocated with the process control computer 41, such as being a part thereof (being stored upon a hard disk or other storage media of the process control computer 41).

As a further alternative, portions of the database and/or redundant copies of the database or redundant portions thereof may be stored in different locations and may be communicated with via either hard wiring or a network, as desired.

The database preferably comprises administrative information 43, rules 44, measurement information 45, and a response history 46, as discussed above.

The response history 46 is a history of usage of the process control system of the present invention and thus comprises a listing of all measurement information received, the rules applied to the measurement information, and the control information sent in response to the measurement information. The response history 46 may be used to analyze performance of the process control system of the present invention, so as to determine the effectiveness and reliability thereof. This is particularly useful in determining the suitability of the rules being used to control a process. Thus, by reviewing the response history 46, it may be possible to modify the rules in a manner which optimizes the process.

The response history 46 may also be used to automate such an optimization process. Prior operation of the process control system 11 of the present invention can optionally be automatically analyzed, such a via the process control computer 41, and the rules then automatically modified so as to effect enhanced operation of the process control system 11.

One example of how the operation of the process control system 11 may be enhanced is by reviewing, either manually or automatically, the response history 46 so as to determine if any trends in process parameters exist. The rules may then be modified so as to take advantage of such trends. For example, if it is determined that the temperature associated with a process always rises undesirably high after it has risen at a certain rate within a certain amount of time, then it may be desirable to reduce the temperature or otherwise compensate therefore sooner than would otherwise be done.

Analysis of the response history 46 may facilitate the mitigation of undesirable lags in response time. As discussed above, when a trend is recognized a response may be initiated earlier than would otherwise occur, so as to better maintain a parameter within a desired range.

Preferably, the process control computer 41 or some device associated therewith has an IP address so as to facilitate communication via the Internet. Optionally, the database 42 also has an IP address.

Figure 8:
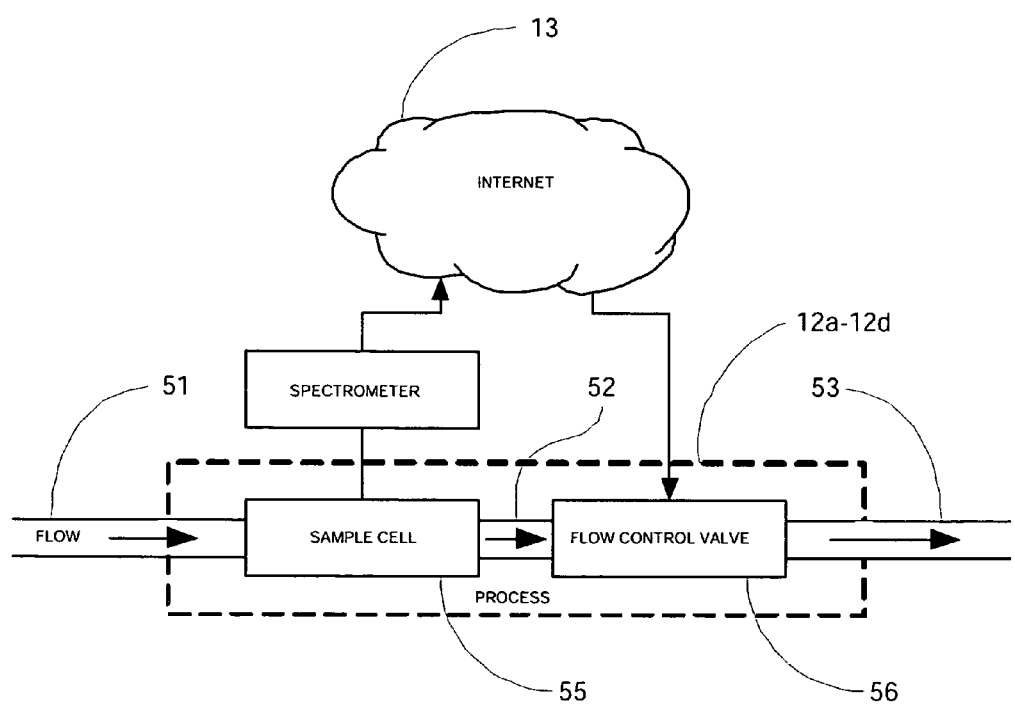
FIG. 8 is a block diagram showing an exemplary process of FIG. 4 in further detail.

Referring now to FIG. 8, an exemplary process 12a-12d is shown. According to this exemplary process, a spectrometer 55 measures the amount or concentration of one or more substances flowing thereto via fluid conduit 51. The spectrometer 55 provides measurement information representative of such measurements to the process control system 11 (FIG. 4) via the Internet 13.

Fluid from the spectrometer 55 flows through fluid conduit 52 to flow control valve 56. The process control system 11 sends control information via the Internet 13 to the flow control valve 56. The flow control valve 56 then responds to the control information from the process control system 11 to modify (increase or decrease), if necessary, the amount of flow exiting therefrom via fluid conduit 53.

More particularly, measurement information from the spectrometer 55 is communicated via the Internet 13 and is received by the process control computer 41 (FIG. 7) of the process control system 11 (FIG. 4). Rules 44 (FIG. 7) from the database 42 are applied to the received measurement information to determine the desired response. For example, if the measurement information from the spectrometer 55 indicates that too much of a substance is flowing through fluid conduit 53, then the rules 44 determine that the desired response is to reduce flow through fluid conduit 53 by reducing flow through flow control valve 56 (by at least partially closing flow control valve 56). Control information which causes control valve 56 to reduce flow therethrough is sent via the Internet 13 from the process control computer 41 to the flow control valve 56 to obtain the desired response.

Thus, the process control system 11 of the present facilitates the control of the rate at which a substance flows through the fluid conduit 53, even though the concentration of the substance within a carrier fluid or solvent varies with time.

As those skilled in the art will appreciate, a computer may be configured to receive the output of the spectrometer 55 and to send measurement information to the process control system 11 via the Internet 13. Similarly, a computer may be configured to receive information from the process control system 11 via the Internet 13 and to provide a control signal to the flow control valve 56 in response thereto. The computer which receives measure information from the spectrometer 55 may be the same computer as the computer which provides control information to the flow control valve 56 or may be a different computer therefrom. That is, one or more computers may be coupled intermediate the spectrometer 55 and the Internet 13, and similarly one or more computers may be coupled intermediate the flow control valve 56 and the Internet 13.

Alternatively, the spectrometer 55 and/or the flow control valve 56 may be configured to communicate directly with the process control system 11 via the Internet, without requiring the use of such intermediate computer(s).

Preferably, the spectrometer 55 and the flow control valve 56 have IP addresses so that they can communicate with the process control computer 41 (FIG. 7) via the Internet. Alternatively, a computer associated with the spectrometer 55 and the flow control valve 56 has an IP address, so that the spectrometer 55 and the flow control valve 56 can communicate with the process control computer 41 via the Internet.

It is understood that the exemplary process control system described herein and shown in the drawings represents only a presently preferred embodiment of the invention. Indeed, various modifications and additions may be made to such embodiment without departing from the spirit and scope of the invention. For example, rather than a hard wired and fiber optic network such as the Internet, the present invention may alternatively utilize radio frequency (RF) connectivity, such as a Bluetooth connection. Indeed, the present invention may comprise any desired combination of hard wired, fiber optic and RF connectivity. Furthermore, the process control computer 41 need not be a general purpose computer, but rather may comprise a dedicated computer, processor or microcontroller.

When it is stated herein that the measurement devices, the control devices and/or the process control system (or the process control computer) have an IP address, it is not necessarily meant that the measurement devices, the control devices and/or the process control system (or the process control computer) themselves must have an IP address, but rather that they are at least associated with a device that has an IP address, such that communication therewith via the Internet is facilitated.

Thus, these and other modifications and additions may be obvious to those skilled in the art and may be implemented to adapt the present invention for use in a variety of different applications.

We claim:

1. A method of securely managing and electronically documenting the configuration, modification of the configuration, and operation of an industrial manufacturing process that is monitored by a measuring device and influenced by a control device, where the configuration comprises rules for collecting and responding to instrument data, the method comprising the steps of:

electronically receiving an input signal containing instrument data from the measuring device;

providing a database management system with a data structure for storing data records relating to user data, configuration data comprising rules for collecting and responding to instrument data, and instrument data that is automatically collected in correspondence with the rules of the configuration data, the user date, the configuration data, and the instrument data being stored in corresponding user data records, configuration data records, and instrument data records; and providing, by a computer, a supervisor application for controlling the database management system, the supervisor application implementing the sub-steps of:

limiting access to the database management system to authorized users based on the user data in the user data records;

allowing an authorized user to modify the configuration data in the configuration data records;

successively storing modifications to the configuration data in the configuration data records, along with an identifier as to the user data record corresponding to the user who modified the configuration data to produce an electronic audit trail of archival configuration data;

receiving the instrument data from the measuring device in accordance with the configuration data in the configuration data records;

successively storing the instrument data received from the measuring device in instrument data records, along with an identifier as to the configuration data record corresponding to the configuration data that was in effect when the instrument data was received, to produce an electronic audit trail of archival instrument data; and outputting control signals to the control device, in accordance with the configuration data in the configuration data records, based on the instrument data received from the measuring device.

2. The method of claim 1 wherein the industrial manufacturing process is a chemical process.

3. The method of claim 1 wherein the industrial manufacturing process is a process governed by 21 CFR, Part 11, promulgated by the United States Food and Drug Administration.

4. The method of claim 1 wherein the measuring device is selected from the group consisting of:

a spectrometer;
a gas chromatograph;
a temperature sensor;
a pressure sensor;
a weight sensor;
an optical sensor;
a timer;
a flow sensor;
a current sensor;
a voltage sensor;
a capacitance sensor;
a inductance sensor;
an electric field sensor;
a magnetic field sensor;
a specific gravity sensor; and
a concentration sensor.

5. The method of claim 1 wherein the control device is selected from the group consisting of:

a valve;
a heater;

a cooler;
a mixer;
a current source;
a voltage source;
an electric field source;
a magnetic field source; and
a laser.

\* \* \* \* \*